United States Patent
Laback et al.

(10) Patent No.: US 7,920,923 B2
(45) Date of Patent: Apr. 5, 2011

(54) BINAURAL STIMULATION IN NEURAL AUDITORY PROSTHESES OR HEARING AIDS

(75) Inventors: Bernhard Laback, Vienna (AT); Piotr Majdak, Vienna (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 439 days.

(21) Appl. No.: 12/143,258

(22) Filed: Jun. 20, 2008

(65) Prior Publication Data

US 2008/0319509 A1    Dec. 25, 2008

Related U.S. Application Data

(60) Provisional application No. 60/945,148, filed on Jun. 20, 2007.

(30) Foreign Application Priority Data

Jun. 20, 2007 (EP) .................................. 07012101

(51) Int. Cl.
*A61N 1/36* (2006.01)

(52) U.S. Cl. .......................................... 607/57
(58) Field of Classification Search ............. 607/57
See application file for complete search history.

(56) References Cited

U.S. PATENT DOCUMENTS

2005/0271222 A1   12/2005   Freed et al. ............... 381/93

FOREIGN PATENT DOCUMENTS

WO    WO02/096153    11/2002

OTHER PUBLICATIONS

Bronkhorst, A. W, et al, "*The effect of head-induced interaural time and level differences on speech intelligibility in noise*", J. Acoust. Soc. Am, vol. 83, No. 4,, Apr. 1988, pp. 1508-1516.
Buell, Thomas N., et al, "*Discrimination of interaural differences of time in the envelopes of high-frequency signals: Integration times*", J. Acoust. Soc. Am., vol. 84, No. 6, Dec. 1988, pp. 2063-2066.
Colburn, H. Steven, et al, "*Binaural Directional Hearing—Impairments and Aids*", Directional Hearing, 1987, pp. 260-278.
Durlach, N. I., et al, "*Binaural Interaction in Impaired Listeners*", Audiology, 20: (1981), pp. 181-211.
Gabriel, Kaigham J., "*Frequency dependence of binaural performance in listeners with impaired binaural hearing*", J. Acoust. Soc. Am,, vol. 91, No. 1, Jan. 1992, pp. 336-347.
Hafter, E. R., et al, "*Detection of interaural differences of time in trains of high-frequency clicks as a function of interclick interval and number*", J. Acoust. Soc. Am, vol. 73, No. 2, Feb. 1983, pp. 644-651.

(Continued)

*Primary Examiner* — Michael Kahelin
(74) *Attorney, Agent, or Firm* — Sunstein Kann Murphy & Timbers LLP

(57) ABSTRACT

The present invention discloses of binaural stimulation in a neural auditory prosthesis. Binaural acoustic signals are generated that represent sound associated with a user's left and right ears respectively. Based on the binaural acoustic signals, corresponding binaural stimulation signals are generated for electrical stimulation of auditory nerve tissue of the user, wherein the binaural stimulation signals each include a fine structure component with periodic characteristics and interaural time difference (ITD) information. A phase jitter component is added to the binaural stimulation signals to reduce the periodic characteristics of the fine structure component while preserving the interaural time difference (ITD) information.

20 Claims, 6 Drawing Sheets

OTHER PUBLICATIONS

Hawkins, David B., et al, "*Interaural Time Discrimination Ability of Listeners with Sensorineural Hearing Loss*", Audiology, vol. 19, (1980), pp. 495-507.

Kaibao, N., et al, "*Encoding Frequency Modulation to Improve Cochlear Implant Performance in Noise*", IEEE Transactions on Biomedical Engineering, vol. 52, No. 1, Jan. 2005, pp. 64-73.

Laback, Bernhard, et al, "*Binaural jitter improves interaural time-difference sensitivity of cochlear implantees at high pulse rates*", PNAS, vol. 105, No. 2., Jan. 15, 2008, pp. 814-817.

Laback, Bernhard, et al, "*Lateralization discrimination of interaural time delays in four-pulse sequences in electric and acoustic hearing*", J. Acoust. Soc. Am, vol. 121, No. 4, Apr. 2007, pp. 2182-2191.

Litvak, Leonid, "*Auditory nerve fiber responses to electric stimulation: Modulated and unmodulated pulse trains*", J. Acoust. Soc. Am, vol. 110, No. 1, Jul. 2001, pp. 368-379.

Macpherson, Ewan, et al, "*Listener weighting of cues for lateral angle: The duplex theory of sound localization revisited*", J. Acoust. Soc. Am, vol. 111, No. 5, Pt. 1, May 2002, pp. 2219-2236.

Majdak, Piotr, "*Effects of interaural time differences in fine structure and envelope on lateral discrimination in electric hearing*", J. Acoust. Soc. Am, vol. 120, No. 4, Oct. 2006, pp. 2190-2201.

Saberi, Kourosh, "*Observer weighting of interaural delays in filtered impulses*", Perception & Psychophysics, 58, (7), 1996, pp. 1037-1046.

Smith, Zachary M., et al, "*Chimaeric sounds reveal dichotomies in auditory perception*", Nature, Mar. 7, 2002; 416(6876), pp. 87-90.

Smoski, Walter J., "*Discrimination of interaural temporal disparities by normal-heairng listeners and listeners with high-frequency sensorineural hearing loss*", J. Acoust. Soc. Am., vol. 79, No. 5, May 1986, pp. 1541-1547.

Stecker, G. C., et al, "*Temporal weighting in sound localization*", J. Acoust. Soc. Am, vol. 122, No. 3, Pt. 1, Sep. 2002, pp. 1046-1057.

Tyler, Richard S., "*Speech perception, localization and laterization with bilateral cochlear implants*", J. Acoust. Soc. Am. vol. 113, No. 3, Mar. 2003, pp. 1617-1630.

Van Hoesel, Richard J. M., "*Sensitivity to binaural timing in bilateral cochlear implant users*", J. Acoust. Soc. Am, vol. 121, No. 4, Apr. 2007, pp. 2192-2206.

Wightman, Frederic L., "*Factors Affecting the Relative Salience of Sound Localization Cues*", Gikey and Anderson, [20], 1997, Chapter 1, pp. 1-23.

Zeng, Fan-Gang, et al, "*Speech recognition with amplitude and frequency modulations*", PNAS, vol. 201, No. 7, Feb. 15, 2005, pp. 2293-2298.

Authorized Officer Dana Schalinatus, *International Search Report and Written Opinion of the International Searching Authority*, International Searching Authority, International Application No. PCT/EP2008/004959, Aug. 25, 2008, 14 pages.

| Subject | Etiology | Age (yr) | Age at Implantation (yr) | | Duration of deafness | | Binaural electrical stimulation experience | Test Electrodes L/R |
| --- | --- | --- | --- | --- | --- | --- | --- | --- |
| | | | L | R | L | R | | |
| CI3 | Meningitis | 24 | 21 | 21 | 2mo | 2mo | 3yr | 4/3 |
| CI8 | Osteogenesis Imperfekta | 44 | 41 | 39 | 3yr | 12yr | 3yr | 7/5 |
| CI10 | Sudden hearing loss | 54 | 44 | 48 | 43yr | 43yr | 6yr | 7/8 |
| CI11 | Temporal bone fracture | 28 | 22 | 22 | 2yr | 2yr | 6yr | 2/3 |
| CI12 | Sudden hearing loss | 40 | 35 | 34 | 8yr | 3yr | 5yr | 2/2 |

FIG. 4

BINAURAL STIMULATION IN NEURAL AUDITORY PROSTHESES OR HEARING AIDS

This application claims priority from European Patent Application EP 7012101, filed Jun. 20, 2007, incorporated herein by reference.

FIELD OF THE INVENTION

The present invention relates to medical implants, and more specifically to binaural stimulation in auditory prostheses systems.

BACKGROUND ART

Binaural stimulation is common in the case of hearing aids, but it has only recently become common in the case of neural auditory prostheses, such as cochlear implants (CI). In the case of cochlear implants, binaural stimulation requires two implants, one in each ear. In the case of cochlear implants or other neural auditory prostheses, the incoming left and right side acoustic signals are similar to those in hearing aids and may simply be the output signals of microphones located in the vicinity of the left and right ear, respectively. However, unlike hearing aids, in neural auditory prostheses, the output is in the form of electrical stimulation signals for directly stimulating auditory nerve tissue. In the following, the discussion with regard to neural auditory prosthesis is focused on cochlear implants for illustrative purposes, but it is to be understood that everything mentioned with specific reference to cochlear implants may equally apply for brain stem implants or modiolar implants, without further mention.

Bilateral cochlear implants provide the benefits of two sided hearing which allows a listener to localize sources of sound in the horizontal plane. That requires information from both ears such as interaural level differences and interaural time differences (ITDs). This is discussed further, for example, in Macpherson, E. A, and Middlebrooks, J. C., *Listener Weighting Of Cues For Lateral Angle: The Duplex Theory Of Sound Localization Revisited*, J. Acoust. Soc. Am. 111, 2219-3622, 2002, which is incorporated herein by reference. An ITD is a relative time shift between signals arriving at the left and right ear which is caused by different times for the signal to reach each ear when the source of sound is not within the median plane. Two-sided hearing also is known to male speech easier to understand in noise, and again the perception of ITD plays a pivotal role therein. This is explained more fully, for example, in Bronkhorst, A. W., and Plomp, R., *The Effect Of Head-Induced Interaural Time And Level Differences On Speech Intelligibility In Noise*, J. Acoust. Soc. Am. 83, 1508-1516, 1988, which is incorporated herein by reference.

In the perception of ITDs, one can distinguish two sources of ITD information, namely ITD information from the envelope of a signal and ITD information from the fine structure of a signal. With reference to FIG. 7, an oscillatory signal can be characterized by its fine structure, i.e. information on the level of the fast varying oscillatory signal 10 and a slowly varying envelope 12. Fine structure information of a signal can, for example, be reflected in the timings of the peaks or zero crossing of the rapidly oscillating signal.

It has been found that of the envelope ITD information and the fine structure ITD information, the latter one plays a more important role for sound localization and for understanding of speech in noise. This has been shown, for example, in Wightman and Kistler, *Factors Affecting The Relative Salience Of Sound Localization Cues* in Binaural and Spatial Hearing in Real and Virtual Environments, edited by Gilkey, R. H., and Anderson, T. R., (Lawrence Erlbaum Associates, Mahwah, N.J., 1997); Smith et al., *Chimaeric Sounds Reveal Dichotomies In Auditory Perception*, in Nature 416, 87-90, 2002; Nie et al., *Encoding Frequency Modulation To Improve Cochlear Implant Performance In Noise*, IEEE Trans. Biomed. Eng. 52, 64-73, 2005; and Zeng et al., *Speech Recognition With Amplitude And Frequency Modulations*, Proc. Natl. Acad. Sci. 102, 2293-2298, 2005, all of which are incorporated herein by reference, 2005, all of which are incorporated herein by reference.

In conventional CIs, fine structure information is not used. Instead, the incoming sound is separated into a number of frequency bands, for each band the slowly-varying envelope is extracted, and this envelope information is used to modulate the amplitude of a high-frequency pulsatile carrier signal. In such conventional CIs, the frequency and phase of the pulsatile carrier signal is simply dictated by the speech processor and not directly related to the fine structure of the incoming signal. Accordingly, with such known CIs, only the envelope ITD information is available, and consequently, ITD perception is very limited.

Recently, CIs have been proposed in which the stimulation signals are comprised of stimulation pulses with a timing that is based on temporal events within the fine structure of the left and right side acoustic signals. For instance, such temporal events could be the peaks or zero crossings within the fine structure of the signal. Stimulation schemes for coding fine structure information have been suggested for example by U.S. Patent Publication 20040478675, U.S. Pat. No. 6,594,525; U.S. Patent Publication 2004136556; which are incorporated herein by reference, and in van Hoesel and Tyler, *Speech Perception, Localization, And Lateralization With Bilateral Cochlear Implants*, J. Acoust. Soc. Am. 113, 1617-1630, 2003; and Litval (et al., *Auditory Nerve Fiber Responses To Electric Stimulation: Modulated And Unmodulated Pulse Trains*, J. Acoust. Soc. Am. 110(1), 368-79, 2001, also incorporated herein by reference. With these improved stimulation strategies, one would have expected that the ITD perception should be increased as compared to stimulation strategies comprising envelope ITD information only. However, in comparative studies no improvement in sound localization or in the understanding of speech in noise environments could be found; See van Hoesel supra.

Hearing aid listeners are also known to have difficulties with localizing sources of sound and understanding of speech in noisy environments. See for example, Colbum, S. et al. *Binaural Directional Hearing—Impairments And Aids* in W. Yost & G. Gourevitch (Eds.), Directional Hearing pp. 261-278, New York: Springer-Verlag, 1987; Durlach N. I. et al., *Binaural Interaction Of Impaired Listeners. A Review Of Past Research* in Audiology, 20(3):181-211, 1981; Gabriel K. J. et al. *Frequency Dependence Of Binaural Performance In Listeners With Impaired Binaural Hearing*, J Acoust Soc Am., Jan: 91(1):336-47, 1992; Hawkins D B, Wightman F L. (1980). Interaural time discrimination ability of listeners with sensorineural hearing loss. Audiology. 19, 495-507; Kinkel, M. et al., *Binaurales Hören bei Normalhörenden und Schwerhörigen I. Meβmethoden und Meβergebnisse*, Audiologische Akustik 6/91, 192-201, 1991; Koelnike, J. et al., *Effects Of Reference Interaural Time And Intensity Differences On Binaural Performance In Listeners With Normal And Impaired Hearing*, Ear and Hearing, 16, 331-353, 1995; and Smoski, W. J. and Trahiotis, C., *Discrimination Of Interaural Temporal Disparities By Normal-Hearing Listeners And Lis-* teners With High-Frequency Sensorineural Hearing Loss, J Acoust Soc Am. 79, 1541-7, 1986, all of which are incorporated herein by reference.

SUMMARY OF THE INVENTION

The present invention discloses of binaural stimulation in a neural auditory prosthesis. Binaural acoustic signals are generated that represent sound associated with a user's left and right ears respectively. Based on the binaural acoustic signals, corresponding binaural stimulation signals are generated for electrical stimulation of auditory nerve tissue of the user, wherein the binaural stimulation signals each include a fine structure component with periodic characteristics and interaural time difference (ITD) information. A phase jitter component is added to the binaural stimulation signals to reduce the periodic characteristics of the fine structure component while preserving the interaural time difference (ITD) information.

In further specific embodiments, the fine structure component may include peaks and/or zero crossings that reflect the ITD information. The phase jitter component may be based on detecting a temporal event in the binaural acoustic signal such as a predetermined time delay-threshold associated with the binaural acoustic signal and/or ITD information from one or more spectral channels associated with the binaural acoustic signal.

Each stimulation signal may include information for multiple spectral channels. And generating the binaural stimulation signals may avoid a time-overlap between pulses from different spectral channels for the same side of hearing. For example, this may specifically be accomplished by at least one of shifting interaural pulse pairs in time within one channel while preserving the associated ITD information, shifting individual pulses while allowing up to some predetermined tolerable amount of change in the ITD information, and canceling one of the pulses or interaural pulse pairs to avoid time-overlap. Preserving the associated ITD information may preferentially preserve lower frequency information over higher frequency information.

Embodiments of the present invention also include a binaural auditory prosthesis. This may include at least one acoustic sensing module for generating binaural acoustic signals representing sound associated with a user's left and right ears respectively. At least one binaural stimulation module generates corresponding binaural stimulation signals based on the binaural acoustic signals for electrical stimulation of auditory nerve tissue of the user, where the binaural stimulation signals each include a fine structure component with periodic characteristics and interaural time difference (ITD) information. At least one interaural time difference (ITD) module adds a phase jitter component to the binaural stimulation signals to reduce the periodic characteristics of the fine structure component while preserving the interaural time difference (ITD) information.

In further specific such embodiments, the fine structure component may include peaks and/or zero crossing that reflect the ITD information. The ITD module may add the phase jitter component based on detecting a temporal event in the binaural acoustic signal such as based on a predetermined time delay-threshold associated with the binaural acoustic signal, and/or based on ITD information from one or more spectral channels associated with the binaural acoustic signal.

Each stimulation signal may include information for multiple spectral channels. The at least one binaural stimulation module may generate the binaural stimulation signals so as to avoid a time-overlap between pulses from different spectral channels for the same side of hearing; for example, by at least one of shifting interaural pulse pairs in time within one channel while preserving the associated ITD information, shifting individual pulses while allowing up to some predetermined tolerable amount of change in the ITD information, and canceling one of the pulses or interaural pulse pairs to avoid time-overlap. The at least one binaural stimulation module may preserve the associated ITD information by preferentially preserving lower frequency information over higher frequency information.

BRIEF DESCRIPTION OF THE DRAWINGS

FIG. 4 is a table of bibliographic data of CI listeners that had been tested for demonstrating the functioning of the invention.

DETAILED DESCRIPTION OF SPECIFIC EMBODIMENTS

Figure 1:
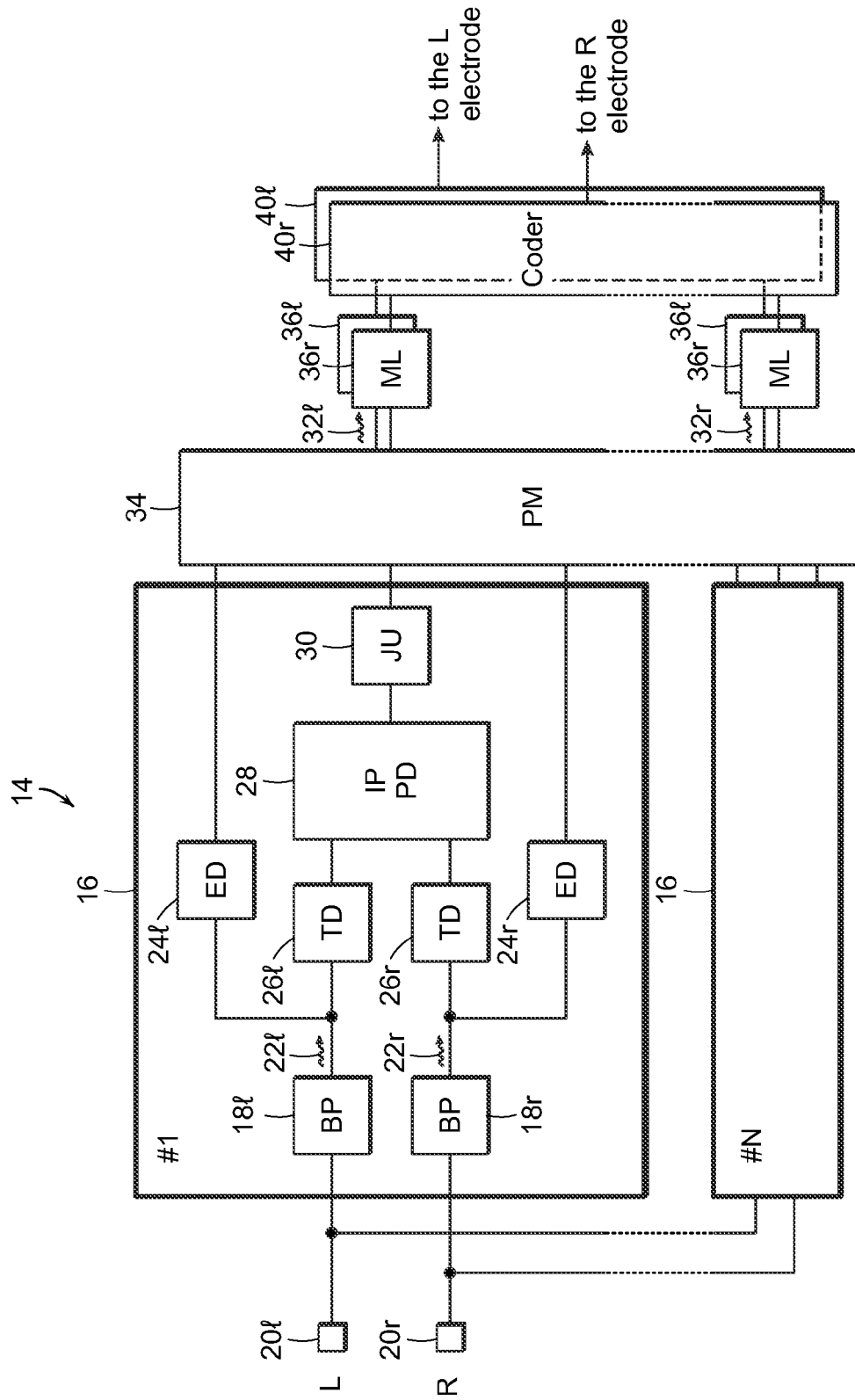
FIG. 1 is a block diagram showing part of a signal processing unit to be used in a cochlear implant according to one embodiment of the present invention.

Embodiments of the present invention provide binaural stimulation in neural auditory prostheses and hearing aids that allows for a better sound localization and/or an improved understanding of speech in the presence of noise.

CI listeners are in principle sensitive to fine structure ITD, but this sensitivity declines at a fine structure rate of a few hundred pulses per second which is considerably lower than the pure tone frequency limit in normal hearing listeners of 1500 Hz.; see, for example, Majdak, P. et al., *Effects Of Interaural Time Differences In Fine Structure And Envelope On Lateral Discrimination In Electric Hearing*, J. Acoust. Soc. Am. 120, 2190-2201, 2006; Laback, B., *Effects Of Interaural Delay In Ongoing Signal, Onset, And Offset In Three Cochlear Implant Listeners*, J. Acoust. Soc. Am 121, 2182-2191, 2007; van Hoesel, *Sensitivity To Binaural Timing In Bilateral Cochlear Implant Users*, J. Acoust. Soc. Am. 121, 2192-2206, 2007, all incorporated herein by reference.

Embodiments of the present invention are based on a hypothesis that the limited fine structure ITD sensitivity is due to a phenomenon called binaural adaptation. Using filtered pulse trains, it has been shown that at higher pulse rates increasing the stimulus duration does not improve ITD sensitivity, and this effect has been referred to as binaural adaptation; cf. Hafter and Dye, *Detection In Interaural Differences Of Time In Trains Of High-Frequency Clicks As A Function Of Interclick Interval And Number*, J. Acoust. Soc. Am. 73(5), 644-651, 1983; and Buell and Hafter, *Discrimination Of Interaural Differences In Time In The Envelopes Of High-Frequency Signals: Integration Times*, J. Acoust. Soc. Am 2063-2066, 1988. In later studies, it was found that binaural adaptation causes high weighting of the onset and low weighting of the ongoing signal; cf Saberi, *Observer Weighting Of Interaural Delays In Filtered Impulses*, Perception and Psychophysics. 58, 1037-1046, 1996; Stecker and Hafter, *Temporal Weighting In Sound Localization*, J. Acoust. Soc. Am. 112(3 Pt 1), 1046-57, 2002; all incorporated herein by reference. Going one step further, it also has been shown that introducing a change in the ongoing signal (a trigger) causes a recovery from binaural adaptation. As a consequence, the portion of the signal following the trigger receives higher weight and this results in an improved ITD sensitivity.

From these findings, embodiments of the present invention are based on the hypothesis that the decreased fine structure ITD sensitivity of CI listeners and hearing impaired listeners could be due to a form of binaural adaptation. Accordingly, embodiments generate binaural acoustic signals that represent sound associated with a user's left and right ears respectively. Based on the binaural acoustic signals, corresponding binaural stimulation signals are generated for electrical stimulation of auditory nerve tissue of the user, wherein the binaural stimulation signals each include a fine structure component with periodic characteristics and interaural time difference (ITD) information. A phase jitter component is added to the binaural stimulation signals to reduce the periodic characteristics of the fine structure component while preserving the interaural time difference (ITD) information. Since binaural adaptation is a phenomenon which occurs for periodic signals, introducing artificial phase jitter into the stimulation signals reduces the periodicities of the signals to make the listener less prone to binaural adaptation. At the same time, the artificial phase jitter of the left and right binaural stimulation signals is synchronized to preserve as much as possible the ITD information contained in the fine structure.

In experimental tests it was found that the introduction of such artificial phase jitter dramatically increased sound localizing capability. This strongly suggests that the hypothesis of the influence of binaural adaptation is correct.

In an auditory prosthesis, the left and right binaural stimulation signals may each be comprised of stimulation pulses the timings of which are based on temporal events detected from the left and right side binaural acoustic signals. This is based on identifying interaural pairs of events among the temporal events, wherein each interaural pair of events is comprised of a temporal event detected from the left side acoustic signal and a temporal event detected from the right side acoustic signal which are attributable to the same acoustic event in the incoming sound but which are generally delayed with respect to each other by an ITD, except, of course, if the source of sound should be located within the median plane. Then, at least some of the pulse timings are manipulated with regard to the timings of the corresponding temporal events such as to reduce the periodicities of the left and right binaural stimulation signals with regard to the periodicities of the left and right side acoustic signals while preserving the ITD between pulses corresponding to ah interaural pair of events. Note that this type of manipulating the pulse timings is a special way of introducing artificial phase jitter to the left and right binaural stimulation signals. Namely, the timings of the pulses do not simply repeat the timings of the temporal events within the fine structure of the left and right side acoustic signals. Instead, the timings of the pulse signal are manipulated such that the pulse train is less periodic than the fine structure of the original left and right side acoustic signals reflecting the incoming sound. However, this manipulation, is performed in such a way that the ITD between pulses corresponding to an interaural pair of events is preserved, such that no ITD information is lost.

In some embodiments, an envelope may be extracted from each of the left and right side acoustic signals, and the stimulation pulses may be generated such that their sizes, in particular their width and/or their height correspond to the respective envelopes.

When pulsatile stimulation signals are used, interaural pairs of events are identified; for example, by determining the time delay between a temporal event within the left side acoustic signal and a temporal event within the right side acoustic signal, judging whether the time delay is below a predetermined delay-threshold, and if the time delay is below the predetermined delay-threshold, identifying the temporal events as an interaural pair of events. For example, the predetermined delay-threshold could be identical to a maximum possible ITD, called $ITD_{max}$ in the following, which corresponds to the distance between a person's ears divided by the speed of sound and is typically between 600 and 700 μs. For channels with low center frequencies, for example center frequencies for which the inverse thereof is more than twice $ITD_{max}$, this way of identifying interaural pairs of events gives unambiguous results: whenever two temporal events in the left and right side acoustic signals are closer in time than $ITD_{max}$, they must form an interaural pair of events. However, for channels with higher frequencies, the period between temporal events will decrease, and then the above mentioned criterion may become ambiguous. Namely, if the center frequency of a given channel is high enough, or, in other words, if the period of the fine structure signal entering that channel is sufficiently short, it is possible that for a given temporal event in the fine structure of the left (right) side signal there are two or more temporal events in the right (left) side signal (one of them prior to and the other after the given temporal event in the left (right) side channel), which are less than a time-delay of $ITD_{max}$ away from the given temporal event in the left (right) side signal. In cases like this, ITD information from one or more channels having lower center frequencies can be used to identify interaural pairs of events. In particular, if in a given channel a first temporal event and a second temporal event exist in one of the left or right side acoustic signals, which are separated in time from a given event in the other one of the left and right side acoustic signals by a first and a second delay, respectively, and both of the first and second delays are smaller than $ITD_{max}$, the first and second delays can be compared with an ITD determined in one or more lower frequency channels, and one of the first and second temporal events can be selected to form an interaural pair of events with the given temporal event based on the comparison. For example, if the comparison should yield that the first delay should match an ITD that has been unambiguously detected in one of the lower frequency channels, then this would indicate that the first temporal event belongs to the same interaural pair of events as the given temporal event.

As mentioned above, if the left and right binaural stimulation signals are pulsatile signals, according to the invention the pulse timings are to be manipulated such as to reduce the periodicity while preserving the ITD between pulses corresponding to an interaural pair of events. According to a preferred embodiment, this manipulation is performed as follows. The left and right binaural stimulation signals are generated such as to comprise interaural pulse pairs constituted by a pulse in the left stimulation signal and a pulse in the right stimulation signal, each corresponding to temporal events within a same interaural pair of events, and such that the time delay between the pulses of each interaural pulse pair is identical with the ITD of the corresponding interaural pair of events. This way, ITD information is preserved. However, at least for some interaural pulse pairs, the time interval between consecutive interaural pulse pairs is varied with regard to the time interval between the corresponding consecutive pairs of events, whereby artificial phase jitter is introduced to the binaural stimulation signals, or in other words, the periodicities thereof are reduced.

The time interval between consecutive interaural pulse pairs may be varied according to a distribution of zero mean and/or limited by a predetermined maximum value of variation $var_{max}$. This maximum value of variation $var_{max}$ is preferably dependent on the channel, and in particular, for at least some of the channels, the maximum value of variation $var_{max}$ is given by a factor k times the period corresponding to the center frequency of the respective channel. Herein, the factor k can be chosen to be 0.125 k 0.9, and preferably 0.5~k<_0.9. As explained later, the effect of phase jitter is mainly achieved for high frequency channels. Thus, it may be advantageous to keep the value k small or even set to 0 for low frequency channels, as phase jitter has little effect at lower rates. Thereby, unnecessary changes in the binaural stimulation signals can be avoided. The value of variation may be a stochastic value selected from a uniform distribution between $\pm var_{max}$. However, deterministic variations are also possible, as long as they are suitable to reduce the periodicity of the pulsatile stimulation signals as compared to the periodicity of the underlying left and right side acoustic signals.

The method is applicable both to stimulation schemes where the binaural stimulation signals of different channels may overlap as well as to stimulation schemes where the stimulation signals are generated such as to avoid a time-overlap between pulses from different channels for the same side of hearing. In the latter case, the method preferably comprises a step of checking whether pulses from different channels for the same side of hearing overlap, and if this is the case, trying first to avoid overlap by shifting interaural pulse pairs in time within one channel while preserving the ITD associated therewith, such that no ITD information will be lost. However, if this is not sufficient to avoid an overlap, next it is tried to shift individual pulses while allowing at most a predetermined tolerable ITD-change to occur, such as to at least limit the loss of ITD information. If this attempt also fails to avoid overlap, one of the pulses or the interaural pulse pairs involved in the overlap are cancelled. In such a scheme to avoid overlap between pulses from different channels for the same side of hearing, in a preferred embodiment ITD preservation in lower frequency channels is preferred over ITD preservation in higher frequency channels.

While the above explanation was focused on embodiments of the invention relating to neural auditory prosthesis, the method of the invention may also be applied to hearing aids. In particular, when adapted for hearing aids, the method may preferably comprise the following steps: generating from the left and right side acoustic signals corresponding left and right fine structure signals reflecting the fine structures thereof and corresponding left and right envelope signals reflecting the envelopes thereof, determining an ITD between the left and right fine structure signals, applying a phase modulation to each of the left and right fine structure signals using modulation signals that are identical except for a relative shift in time by the amount of the ITD, and combining the modulated left and right fine structure signals with the left and right envelope signals respectively, such as to obtain the left and right binaural stimulation signals.

By applying a phase modulation to each of the left and right fine structure signals, the periodicity of the left and right fine structure signals can be reduced with regard to the original left and right fine structure signals, which will avoid or at least reduce the effect of binaural adaptation and thus to avoid the above mentioned negative consequences thereof. It is to be understood that this type of phase modulation is a further way of introducing artificial phase jitter into the binaural stimulation signals. At the same time, the artificial phase jitter of the left and right binaural stimulation signals is synchronized such as to preserve the ITD information because the same modulation signals are used for a phase modulation of the left and right fine structure signals except for a relative shift in time by the amount of the ITD signal. Therefore, although artificial jitter is introduced to the left and right binaural stimulation signals, no ITD information is lost. Instead, due to the reduced periodicity of the binaural stimulation signals, the listener's sensitivity for the ITD information is increased by avoiding binaural adaptation.

For promoting and understanding the principles of the invention, reference will now be made to the preferred embodiments illustrated in the drawings, and specific language will be used to describe the same. It will nevertheless be understood that no limitation of the scope of the invention is thereby intended, such alterations and further modifications in the illustrated device and method, and such further applications of the principles of the invention as illustrated therein being contemplated as would normally occur now or in the future to one skilled in the art to which the invention relates.

In the following, with reference to FIGS. 1 to 6, embodiment of the invention are described with specific reference to cochlear implants (CI). It is understood, however, that the same principles and most of the features of the signal processing unit equally apply for other types of neural auditory prosthesis, such as auditory brain stem implants or modiolar implants. Also, the principles of the invention equally apply for hearing aids, and an example of such an embodiment will be discussed below with reference to FIG. 8.

With reference to FIG. 1, a block diagram of a signal processing unit 14 is shown. This block diagram 14 may be based on a suitably programmed digital signal processor, a field programmable gate array, or an application specific integrated circuit.

The signal processing unit 14 includes a number of N subunits 16 which are essentially identical, and of which only the first one is shown in detail and the Nth one is indicated, while the remaining subunits are omitted for clarity of the illustration. Each of the subunits 16 comprises two bandpass filters, 18*l* and 18*r* which are each connected to receive an incoming signal detected by microphones 20*l*, 20*r* located in the vicinity of the left and right ears, respectively. Note that the illustration of FIG. 1 is limited to the components essential for promoting an understanding of the invention, and that a number of conventional components such as analog front end circuitry, A/D converters or automatic gain control have been omitted from the block diagram to focus on the essential features.

Figure 7:
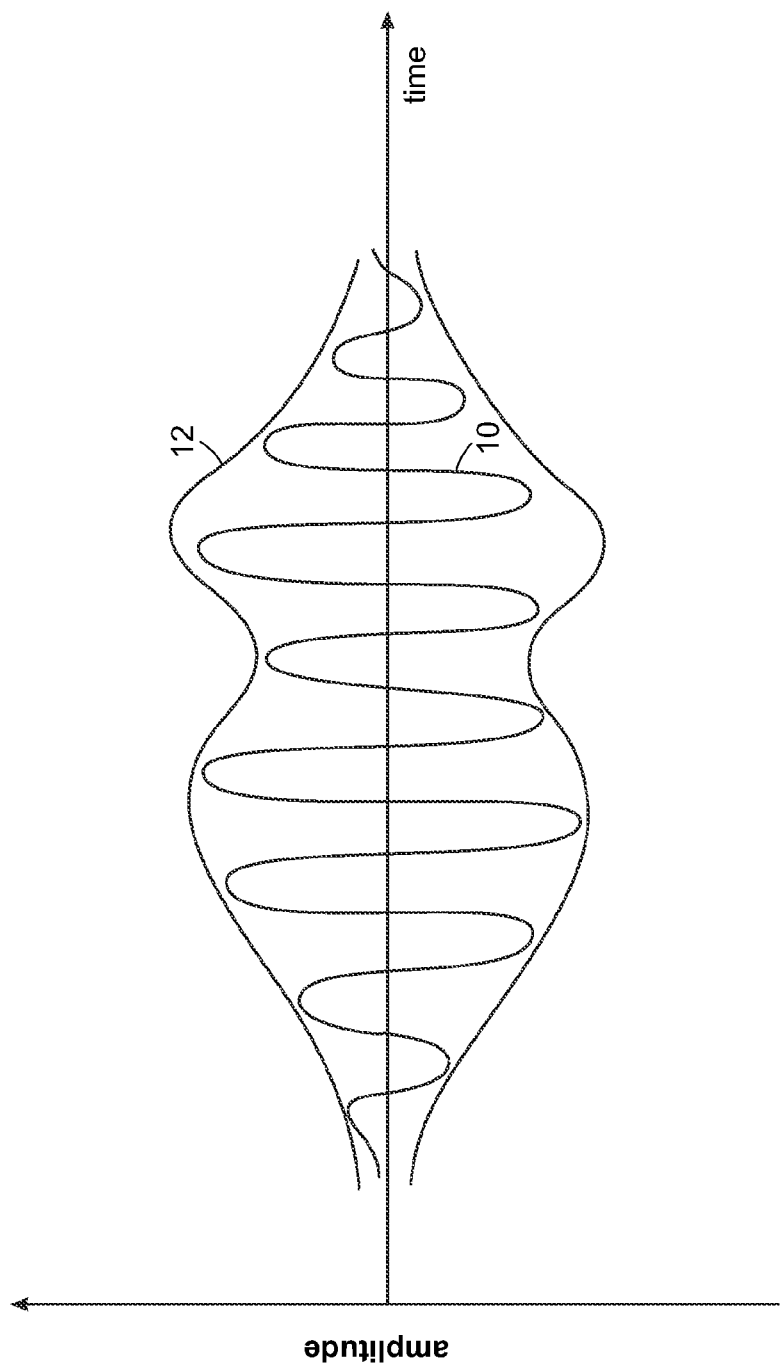
FIG. 7 is a schematic diagram showing a signal displaying slowly varying envelope information and rapidly varying fine structure information.

The bandpass filters 18*l*, 18*r* only pass a spectral portion of the total sound signal detected at the left and right ears, respectively, which is in the vicinity of a center frequency of the bandpass filters 18*l*, 18*r*. Accordingly, the subunit 16 shown in detail in FIG. 1 resembles a spectral channel, and the other subunits which are not shown in detail in FIG. 1 resemble further spectral channels at mutually different bandpass filter center frequencies. The bandpass filters 18*l*, 18*r* output a left side signal 22*l* and a right side signal 22*r*, respectively which are symbolically indicated in FIG. 1. The left and right side acoustic signals 22*l*, 22*r* are input into corresponding envelope extractors 24*l*, 24*r* and timing detectors 26*l*, 26*r*, respectively. The envelope extractors 24*l*, 24*r* are adapted to extract the envelope information of the left and right side acoustic signals 22*l*, 22*r*, respectively The timing detectors 26*l*, 26*r* are adapted to detect the timing of temporal events within the fine structure of the left and right side acoustic signals 22*l*, 22*r*, respectively. For example, with reference to FIG. 7 these temporal events could be the peaks of the fine structure signal 10, or could be the zero crossings thereof. The timing detectors 26*l*, 26*r* are both connected with an interaural pulse pair detector 28 which serves to identify interaural pairs of events among the temporal events detected by the timing detectors 26*l*, 26*r*.

An interaural pair of events is a pair of events comprised of a temporal event detected from the left side signal 22*l* and a temporal event detected from the right side signal 22*r* which are attributable to the same acoustic event in the incoming sound but which are generally delayed with respect to each other by an interaural time difference (ITD). That is to say, if the source of sound was located in the median plane, interaural pairs of events would simply be comprised of temporal events within the left and right side acoustic signals 22*l*, 22*r* which are simultaneous in time. However, if the source of sound is away from the median plane, the left and right side acoustic signals 22*l*, 22*r* are shifted in time with respect to each other by an ITD which is caused by a difference in the distance between the left ear and the source of sound on the one hand and the distance between the right ear and the source of sound on the other hand. This ITD is reflected both, in a temporal shift of the envelope as well as in a temporal shift between corresponding temporal events within the fine structure of the left and right side acoustic signals 22*l*, 22*r*. These corresponding temporal events form the above mentioned interaural pairs of events, and it is the duty of the interaural pulse pair detector 28 to identify interaural pairs of events among the temporal events detected by the timing detectors 26*l*, 26*r*.

The interaural pulse pair detector 28 is connected with a jitter unit 30 which is adapted to introduce phase jitter into the left and right binaural stimulation signals 32*l*, 32*r*, respectively. In particular, the jitter unit 30 is configured to generate or modify pulse timings for stimulation pulses of the left and right binaural stimulation signals 32*l*, 32*r* from or with regard to the timings of the detected temporal events within the fine structure of the left and right side acoustic signals 22*l*, 22*r* such that the modified pulse timings are less periodic than the corresponding temporal events in the fine structure of the left and right side acoustic signals 22*l*, 22*r* while preserving the ITD between pulses corresponding to an interaural pair of events, which have been detected by the interaural pulse pair detector 28. A more detailed explanation of the function of the interaural pulse pair detector 28 and the jitter unit 30 will be given below with reference to FIGS. 2 and 3. For each subunit 16, or in other words, for each channel, the envelope detectors 24*l*, 24*r* and the jitter unit 30 are connected to a pulse management unit 34. The pulse management unit 34 receives the envelope information from the left and right envelope detectors 24*l*, 24*r* and the pulse timing information from the jitter unit 30 and therefrom generates pulsatile left and right side binaural stimulation signals 32*l*, 32*r*.

The binaural stimulation signals 32*l*, 32*r* are input into maplaw units 36*l*, 36*r* in which the binaural stimulation signals are scaled or amplified in a way that the size of each signal is adapted to promote the wanted hearing sensation of the individual CI listener. The left and right side binaural stimulation signals 32*l*, 32*r*, after being modified in the maplaw units 36*l*, 36*r*, are input into a corresponding coder 40*l*, 40*r* which generates the current signals corresponding to the pulsatile stimulation signals that are to be applied to the electrodes of the implant (not shown).

A significant difference between the signal processing unit 14 of FIG. 1 and signal processing means of ordinary CIs is that the same signal processing unit 14 is used for generating both, the left and right binaural stimulation signals 32*l*, 32*r*. This is due to the fact that the artificial jitter introduced to the binaural stimulation signals 32*l*, 32*r* has to be synchronized between left and right binaural stimulation signals 32*l*, 32*r*, such that the ITD information is preserved, and for this synchronization it is most convenient if the signal processing of the left and right binaural stimulation signals 32*l*, 32*r* takes place in the same signal processing unit, for example in a suitably programmed digital signal processor. This is of course different from ordinary CIs in which the binaural stimulation signals are independent of each other and are therefore generated by two entirely separated signal processing units, often called "speech processors", which are separately provided for the left and right ear. In one embodiment of the present invention, the common signal processing unit 14 will be located behind one of the ears. This means of course that one way or the other the stimulation signal for the other ear must be transferred to the electrode within the other ear. This can be achieved in a number of different ways, and a specific choice is not critical to the invention.

For example, it would be possible to provide the maplaw units 36*l*, 36*r* and the coders 40*l*, 40*r* in the vicinity of the corresponding ear. In such case, one of the binaural stimulation signals 32*l*, 32*r* has to be transferred to the ear that is remote to the signal processing unit 14, for example by radiofrequency transmission or via a signal cable that is implanted under the user's skin. In this case, the interface between common circuitry and the circuitry for the individual ears would lie between the pulse management unit 34 and the maplaw units 36*l*, 36*r*. However, this interface could also be between the maplaw units 36*l*, 36*r* and the coder 40*l*, 40*r*, or even after the coders 40*l*, 40*r*. Also, the embodiment shown in FIG. 1 could be modified such that two signal processing units are used, one provided in the vicinity of each ear. In such a case, the two signal processing units would have to be communicatively coupled such as to allow the detection of interaural pairs of events and to generate synchronized jitter.

Figure 2:
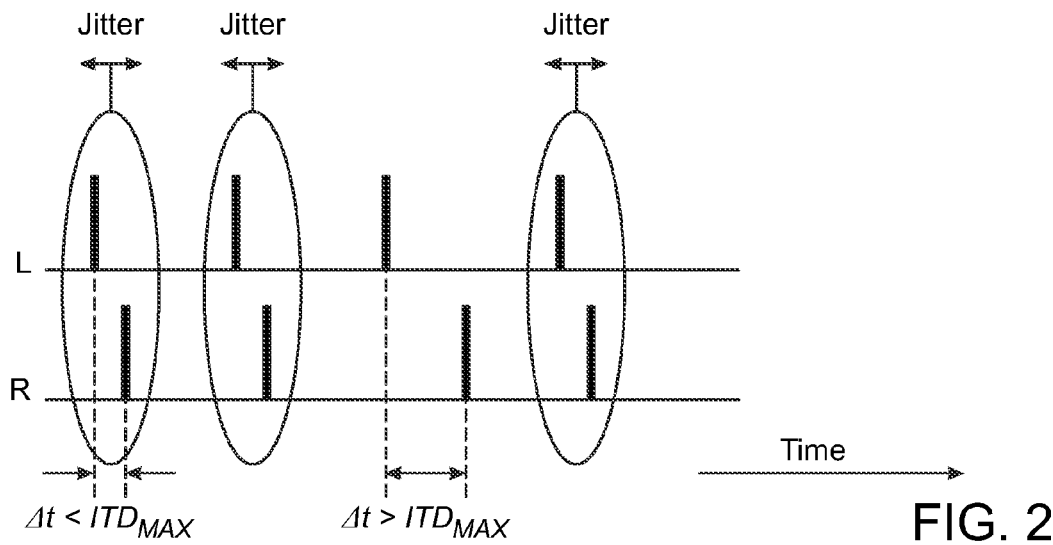
FIG. 2 is a schematic diagram illustrating pulse trains resembling temporal events within the fine structure of a left side and a right side signal and in particular identifies interaural pairs of events.
Figure 3A:
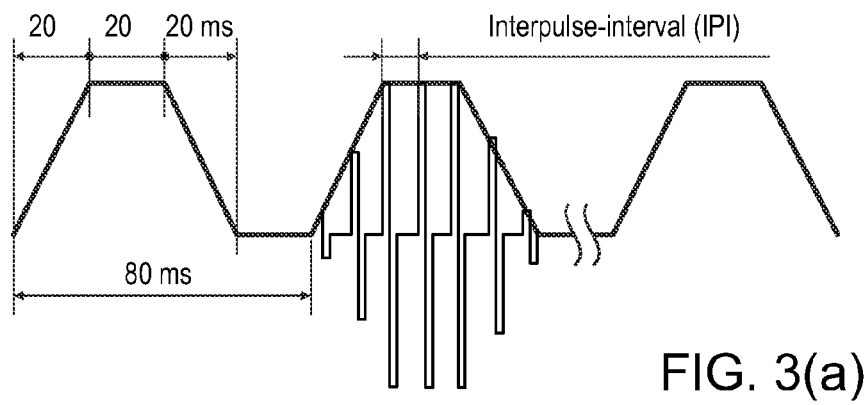
FIG. 3(a) illustrates a stimulation signal for use in a cochlear implant having a trapezoidal amplitude modulation forming the envelope for a pulsatile signal reflecting the fine structure of incoming sound.

Next, with reference to FIGS. 2 and 3, the functioning of the interaural pulse pair detector 28 and the jitter unit 30 will be explained in more detail. First of all, please refer to the upper two panels of FIG. 3(*b*) showing a pulse train which corresponds to the temporal events within the fine structure of the left and right side acoustic signals 22*l*, 22*r*, respectively. As mentioned before, these temporal events can be the peaks or zero crossings within the fine structure of the left and right side acoustic signals. Since the temporal events within the fine structure of the left and right side acoustic signals are periodic, the pulse train is periodic as well, with a constant or nearly constant interpulse interval.

Figure 3B:
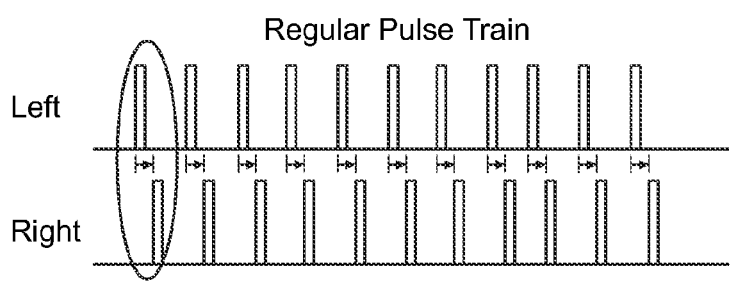
FIG. 3(b) shows in the upper two panels the pulse timings of the left and right stimulation signals if no artificial jitter is provided thereto. The lower two panels of FIG. 3(b) show the pulse timings of left and right stimulation signals that are provided with artificial phase jitter that is synchronized between the left and right signals such as to preserve the ITD information.
Figure 3B:
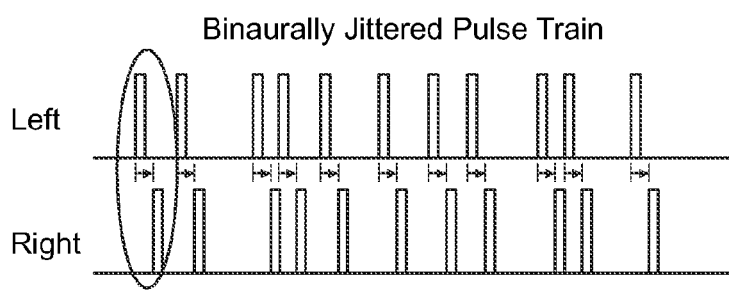

As can further be seen, the temporal events within the fine structure of the left and right side acoustic signals come in pairs called interaural pairs of events herein of which an exemplary one is encircled in FIG. 3(b). The temporal events within a pair are delayed with respect to each other by the ITD (which is indicated by the small arrows in FIG. 3(b)). In the specific example of FIG. 3(b) the left event is always earlier than the right event of the same interaural pulse pair, which means that the source of sound is closer to the left ear than the right ear. If the listener is sensitive to the ITD information he or she can localize the source of sound, that is he or she can tell that the sound is coming from a direction more to the left than to the right.

As mentioned above, one would have assumed that introducing this fine structure ITD information in CIs would help CI listeners to localize sound and to also increase understanding of speech in noise. Since the pulses shown in FIG. 3(b) represent the timing of the temporal events, the obvious way to introduce fine structure information in CIs would be to use this timing for the stimulation pulses for the electrodes within the implant (modulo of course, a global time offset needed for the signal processing), and this is what has in fact been done in prior applications. However, as also mentioned in the introductory part, in actual experiments with CI listeners this positive effect could not be found. This reflects an assumption that CI listeners are sensitive to fine structure ITD information in principle, but that especially at high frequencies essential for understanding speech the sensitivity to the ITD information is greatly hampered by the above mentioned phenomenon of binaural adaptation which in turn has to do with the periodicity of the fine structure signal. Accordingly, if the periodicity of the fine structure signal can be somewhat reduced, then the effects of binaural adaptation would be avoided and consequently the CI listener would be more sensitive to the fine structure ITD information. In other words, the periodicity of the fine structure is artificially reduced as reflected in the binaural stimulation signals, and an artificial phase jitter is introduced into the binaural stimulation signals.

In case of a pulsatile signal, introducing phase jitter would amount to shifting some or all of the pulses with regard to the periodic timing. However, if this shifting would be done independently for the left and right binaural stimulation signals, the fine structure ITD information would be greatly reduced or even be completely lost. Instead, according to an embodiment of the invention the pulse timings are shifted pairwise such that the ITD within each interaural pulse pair is preserved, as is shown in the lower two panels of FIG. 3(b). Since the pulse timings are shifted pairwise, the phase jitter introduced to the stimulation signal is synchronized between the left and right binaural stimulation signals.

One step in the manipulation of the pulse timings is to identify interaural pairs of events. This is explained in more detail with reference to FIG. 2. In FIG. 2, temporal events in the left and right side signal are indicated by a left pulse train (upper panel) and a right pulse train (lower panel). These pulses do not yet resemble the stimulation pulses but instead only reflect the timings of temporal events within the fine structure of the left and right side acoustic signals $22l$, $22r$ as detected by the timing detectors $26l$, $26r$. In general, interaural pairs of events or interaural pulse pairs can be detected by determining the time delay between a temporal event within the left side signal and a temporal event within the right side signal. If this time delay is less than a maximum possible ITD, called $ITD_{max}$ in the following, the two temporal events are identified as belonging to the same interaural pair of events, and the corresponding pulses form an interaural pulse pair. Then the jitter unit 30 can shift interaural pulse pairs with respect to each other such as to introduce jitter into the pulsatile stimulation signal while preserving the ITD information. In FIG. 2, three such interaural pairs of events are indicated by being encircled. However, the two pulses which are not encircled are separated in time by more than $ITD_{max}$ and can therefore not belong to an interaural pair of events. Note that the value of $ITD_{max}$ corresponds to the distance between the ears of the listener divided by the speed of sound and is typically about 600 μs to 700 μs.

In channels with low frequencies, the interpulse intervals will be much longer than $ITD_{max}$, and accordingly, there will be no ambiguity in the identification of interaural pairs of events. That is to say, whenever two pulses or two events are separated in time by less than $ITD_{max}$ they must be part of an interaural pair of events. However, for channels with higher frequency, the interpulse intervals may become so short that a situation arises in which for a given temporal event in one of the left and right side acoustic signals, there exist a first and a second temporal event in the other one of the left or right side acoustic signals which are both separated in time from the given signal by a first and a second delay respectively which are both smaller than $ITD_{max}$. In cases like this, ITD information from lower frequency channels can be used to resolve the ambiguity. In particular, the interaural pulse pair detector 28 compares the first and second delay with ITD values from one or more lower frequency channels, in which the ITD is known to be determined correctly. Then, if it turns out that one of the first or second time delays corresponds with the ITD from the lower frequency channel, the corresponding first and second temporal event is selected to form an interaural pair of events with the given temporal event. So by using information from lower frequency channels, the interaural pulse pair detector 28 is capable of identifying interaural pairs of events even in higher frequency channels, where ambiguities may arise.

After interaural pairs of events are identified by the interaural pulse pair detector, the jitter unit 30 can then introduce artificial phase jitter into the left and right binaural stimulation signals by varying the time interval between consecutive interaural pulse pairs (also called interpulse intervals in the following) with regard to the time interval between the corresponding consecutive pairs of events. For example, the jitter unit 30 can vary the interval between consecutive interaural pulse pairs according to a distribution of zero mean and limited by a predetermined maximum value of variation $var_{max}$. In the shown embodiment, the maximum value of variation $var_{max}$, is dependent on the channel, and in particular it is given by a factor k times the period corresponding to the interpulse interval of the respective channel. Preferable values of k range between $0.5 < k < 0.9$, but experiments showed that even for variations as small as $k=0.125$ a noticeable improvement in ITD sensitivity was obtained. The value of variation of the interpulse interval may be a stochastic value selected from a distribution between $\pm var_{max}$, but a deterministic variation is also possible.

As mentioned before, the pulse manager 34 of FIG. 1 is adapted to combine the timings of the stimulation pulses with the envelope information received from the envelope detectors $24l$, $24r$ to generate signals comprised of pulses with sizes determined by the envelope. An example of a final pulsatile stimulation signal is shown in FIG. 3(a) having a slowly varying trapezoidal envelope and a fine structure comprised of biphasic stimulation pulses.

In some CIs, a time overlap of stimulation pulses from different channels for the same side of hearing is to be avoided. This can also be achieved under the control of the pulse manager 34. The pulse manager 34 checks whether stimulation pulses from different channels for the same side of hearing would overlap, and if this is the case, it tries to avoid the overlap by shifting interaural pulse pairs in time within one channel while preserving the ITD associated therewith. That is to say, the first attempt is to simply choose a different variation of interpulse interval to avoid the overlap. If this is not sufficient, the pulse manager 34 next attempts to shift individual pulses while allowing at most a predetermined tolerable ITD change to occur. However, if this is not possible as well, one of the pulses or interaural pulse pairs involved in the overlap are simply cancelled.

Next, some examples of tests of the method are given. The tests have been performed with assistance of five listeners which were binaurally supplied with MED-EL cochlear implants (Combi 40+). All listeners were post-lingually deafened, have high speech recognition scores and at least three years of binaural CI experience at the time of the tests. Bibliographic data are provided in Table 1. Left/right discrimination of a target sound containing ITD was tested in comparison to a preceding reference stimulus with zero-ITD. Visual response feedback was provided after each trial. Listeners were trained on the task for a couple of hours before starting formal data collection. For the binaural stimulation signals, 300 ms trains of biphasic electric pulses with trapezoidal amplitude modulation as shown in FIG. 3($a$) were used. They were presented binaurally and had an ITD in the entire waveform. Periodic pulse trains (upper part of FIG. 3($b$)) had a constant interpulse interval (IPI), while binaurally-jittered pulse trains (lower part of FIG. 3($b$)) had randomly jittered IPIs. In particular, in the jittered stimulation signals, the time interval between consecutive interaural pulse pairs were varied according to a rectangular zero mean distribution with a total width of k times the period corresponding to the center frequency of the channel. That is, for k=1 the largest possible IPI is twice the nominal interpulse-interval. The independent variables in the tests were k (0.125, 0.25, 0.5, 0.75, and 0.9), the pulse rate (400, 800, 938, 1082, and 1515 pulses per second (pps)) and the interaural time difference (100, 200, 400, and 600 µs). Binaural stimuli were presented at an interaural electrode pair, which was chosen to elicit equal pitch on both sides.

Figure 5:
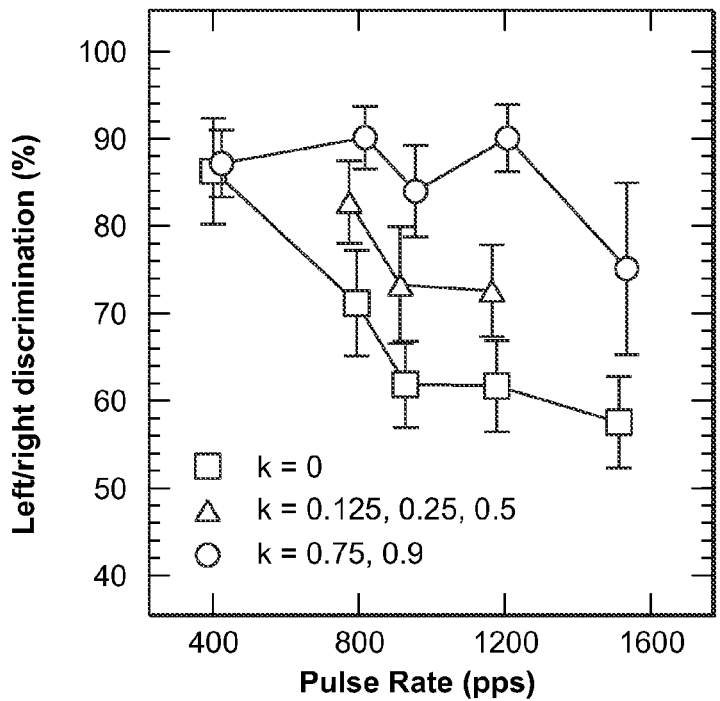
FIG. 5 is a diagram showing the percent correct score (Pc) as a function of the pulse rate obtained in tests with the CI listeners of the table of FIG. 4.

FIG. 5 shows the percentage of correct left/right discrimination (Pc) as a function of pulse rate, averaged over the listeners and the three ITD values 200, 400, and 600 µs. Different amounts of jitter were tested, as given by the parameter k, and the results were pooled into a large jitter (k=0.75 and 0.9, circles) and small jitter (k=0.125, 0.25, and 0.5, triangles). The error bars represent 95% confidence intervals. At the lowest pulse rate tested (400 pps), Pc is generally high and does not differ between the conditions with and without binaural jitter. At the higher pulse rates (>400 pps), however, there is a large difference between the results for the periodic condition and the binaurally-jittered conditions. For the periodic condition (k=0, squares in FIG. 5) Pc decreases sharply with increasing pulse rate and even approaches the range of chance performance. In contrast to this, the conditions with binaural jitter show large improvements compared to the periodic condition. For large jitter, the performance remains constantly high up to 1182 pps and declines at 1515 pps, even though significantly above the periodic condition. For small jitter, improvements are about half of those for large jitter. So this demonstrates that in fact by introducing the artificial phase jitter into the stimulation signal, the localization of sound is greatly improved.

In fact, the decline in performance within increasing pulse rate for the periodic condition is consistent with previous studies (van Hoesel and Tyler, *Speech Perception, Localization, And Lateralization With Bilateral Cochlear Implants*, J. Acoust. Soc. Am. 113, 1617-1630, 2003; Majdak et al., *Effects Of Interaural Time Differences In Fine Structure And Envelope On Lateral Discrimination In Electric Hearing*, J. Acoust. Soc. Am. 120, 2190-2201, 2006; Laback et al., *Effects Of Interaural Delay In Ongoing Signal, Onset, And Offset In Three Cochlear Implant Listeners*, J. Acoust. Soc. Am 121, 2182-2191, 2007). At 400 pps, performance seems not to be limited by binaural adaptation and hence no improvement by applying binaural jitter can be expected. At higher pulse rates, such as above 800 pps, however, binaural adaptation seems to severely limit fine structure ITD sensitivity. Ongoing envelope ITD appears to have contributed little at all rates tested.

The results clearly show that introducing binaural jitter makes CI listeners sensitive to fine structure ITD at rates up to at least 1515 pps. Thus, binaurally jittered stimulation resolves the discrepancy in the rate limitation between CI listeners and normal hearing listeners. Overall, the finding of strong improvements by adding binaural jitter at higher pulse rates but not at lower rates indicates that an excessive form of binaural adaptation limits the fine structure ITD sensitivity at higher pulse rates. Thus, introducing ongoing temporal changes in the stimulus, as it is done in the method of the invention, causes recovery from binaural adaptation in CI listeners.

Figure 6:
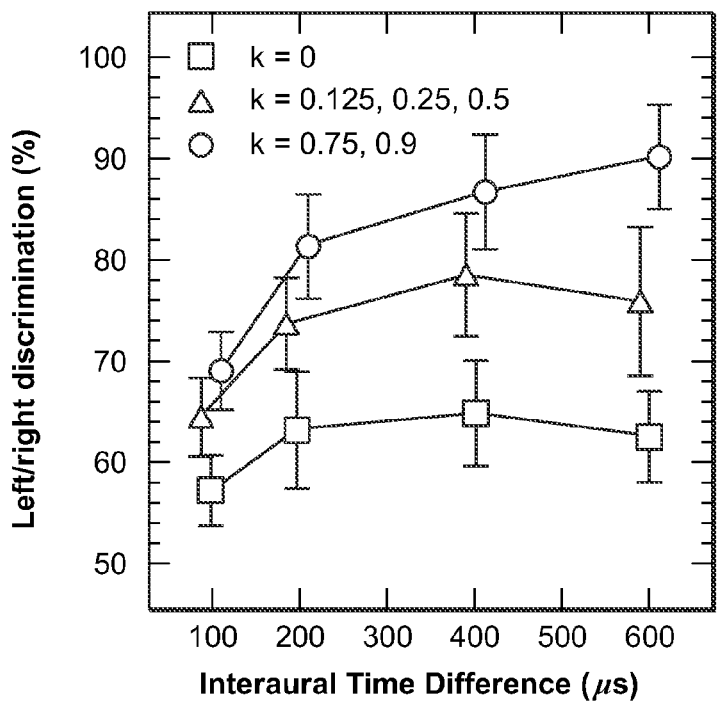
FIG. 6 is a diagram showing the percent correct score (Pc) as a function of the interaural time difference obtained from tests with the CI listeners of the table of FIG. 4.

In FIG. 6, the percent correct score (Pc) as a function of the interaural time difference is shown. The periodic condition without binaural jitter (k=0) is depicted by squares, the condition with small jitter (k=0.125, 0.25, and 0.5) is depicted by triangles and the condition with large jitter (k=0.75, and 0.9) is depicted by circles. The data are averaged over all five subjects and the pulse rates 800, 938, 1082 and 1515 pps, for which the periodic condition has a low Pc. The error bars represent 95% confidence intervals. As can be seen from FIG. 6, for the periodic condition, Pc is constantly low at all ITD values. For the conditions with binaural jitter, however, Pc increases monotonically with the ITD. The improvements by binaural jitter are significant already at the smallest ITD of 100 µs and increase further with increasing ITD. So again, this demonstrates that by introducing artificial phase jitter to the stimulation signal, the sensitivity with regard to fine structure ITD information at high frequencies is greatly enhanced, which allows CI listeners to much better localize sound than without such jitter. This will also improve the understanding of CI listeners of speech in noise.

Figure 8:
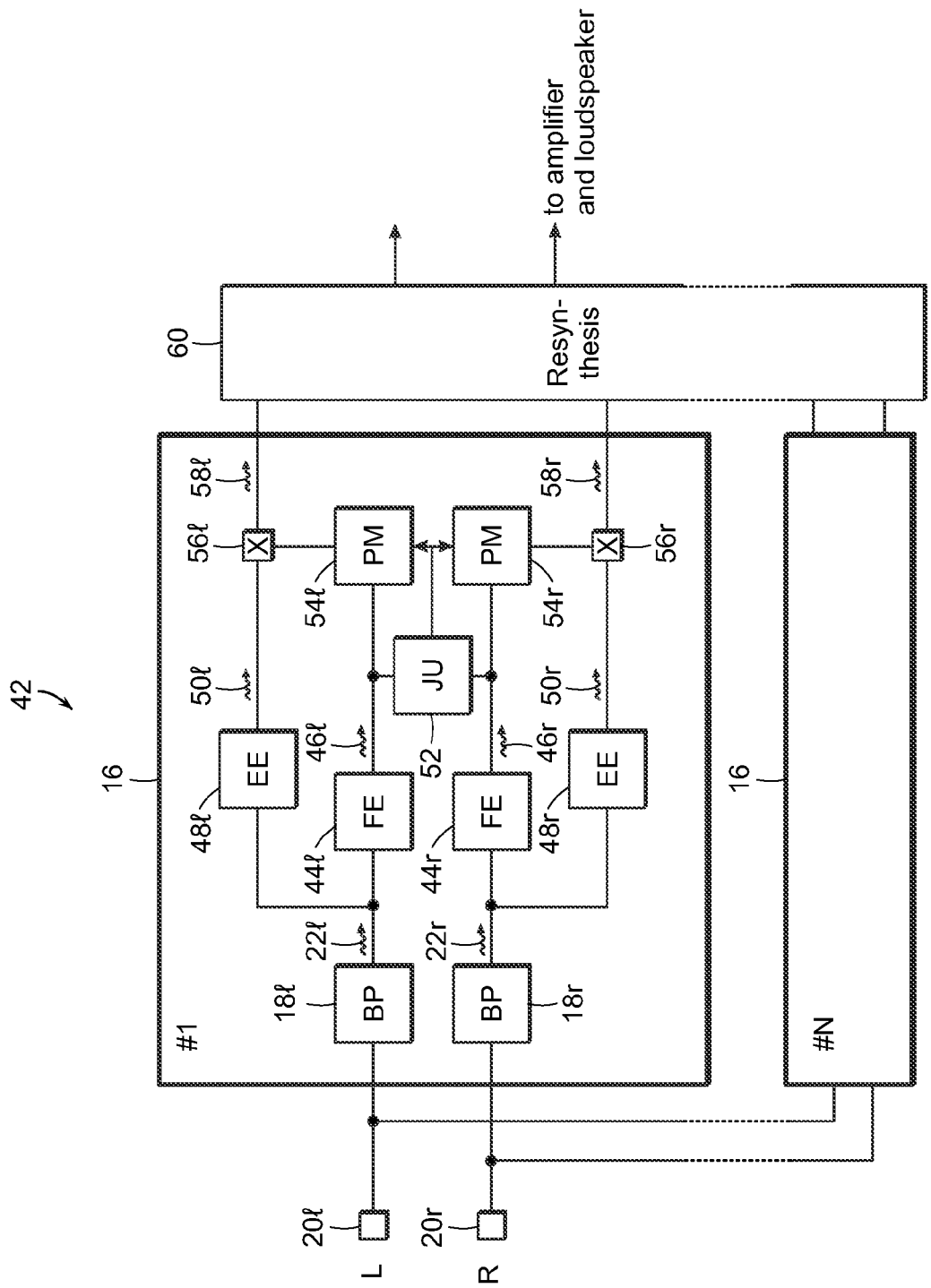
FIG. 8 is a block diagram showing a signal processing unit for the use in hearing aids according to one embodiment.

While the method has been described in detail with reference to neural prostheses such as CIs, it may equally well be applied for stimulation signals in hearing aids. An embodiment of a signal processing unit 42 for use in hearing aids is shown in FIG. 8. The signal processing unit 42 of FIG. 8 is in many regards similar to the signal processing unit 14 of FIG. 1, and therefore, identical components are denoted with identical reference signs, and the description thereof is not repeated.

Similar as to FIG. 1, an incoming left and right signal is bandpass filtered by bandpass filters 18$l$, 18$r$ to generate left and right side acoustic signals 22$l$, 22$r$ respectively. The left side signal 22$l$ is input into a fine structure extractor 44$l$ for extracting a rapidly varying fine structure signal 46$l$, and to an envelope extractor 48$l$ for extracting a slowly varying envelope signal 50$l$. In a similar way, a right fine structure signal

46r and a right envelope signal 50r is generated from the right side signal 22r by using the corresponding fine structure extractor 44r and envelope extractor 48r, respectively.

A jitter unit 52 receives the left and right fine structure signals 46l, 46r and determines the ITD associated therewith in one of the ways per se known to the person skilled in the art. Then, the fine structure signals 46l, 46r are phase modulated by a phase modulator 54l, 54r such as to introduce artificial phase jitter into the left and right fine structure signals 46l, 46r, respectively. This modulation is done, however, in a way such that the ITD information contained in the fine structure signals 46l, 46r is preserved or at least nearly preserved. This can for example be done by using the same modulation signal for the phase modulators 54l, 54r, but with a relative shift in time between the modulation signals by the amount of the ITD determined by the jitter unit 52.

Next, the phase-modulated fine structure signals are combined with the corresponding envelope signals 50l, 50r, for example by multipliers 56l, 56r to obtain binaural stimulation signals 58l, 58r. Unlike the embodiment of FIG. 1, where the binaural stimulation signals 32l, 32r were pulsatile signals, here the binaural stimulation signals 58l, 58r are wave signals for generating sound waves to be injected to the respective ear. The left and right binaural stimulation signals 58l, 58r of different channels are resynthesized by resynthesizing means 60 and then output to the left and right ear amplifiers and loudspeakers.

With the signal processing unit 42 of FIG. 8, similar effects as specifically demonstrated for CI listeners are expected, as the artificial jitter introduced into the binaural stimulation signals 58l, 58r again helps to avoid binaural adaptation which would decrease ITD sensitivity for listeners with hearing impairment as well.

Embodiments of the invention may be implemented in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g. the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of binaural stimulation in a neural auditory prosthesis, the method comprising:
   generating binaural acoustic signals representing sound associated with a user's left and right ears respectively;
   generating corresponding binaural stimulation signals based on the binaural acoustic signals for electrical stimulation of auditory nerve tissue of the user, wherein the binaural stimulation signals each include a fine structure component with periodic characteristics and interaural time difference (ITD) information; and
   adding a phase jitter component to the binaural stimulation signals to reduce the periodic characteristics of the fine structure component while preserving the interaural time difference (ITD) information.

2. A method according to claim 1, wherein the fine structure component includes peaks reflecting the ITD information.

3. A method according to claim 1, wherein the fine structure component includes zero crossings reflecting the ITD information.

4. A method according to claim 1, wherein the phase jitter component is based on detecting a temporal event in the binaural acoustic signal.

5. A method according to claim 4, wherein detecting the temporal event is based on a predetermined time delay-threshold associated with the binaural acoustic signal.

6. A method according to claim 4, wherein detecting the temporal event is based on ITD information from one or more spectral channels associated with the binaural acoustic signal.

7. A method according to claim 1, wherein each stimulation signal includes information for a plurality of spectral channels.

8. A method according to claim 7, wherein generating the binaural stimulation signals avoids a time-overlap between pulses from different spectral channels for the same side of hearing.

9. A method according to claim 8, wherein avoiding time-overlap includes:
   at least one of shifting interaural pulse pairs in time within one channel while preserving the associated ITD information, shifting individual pulses while allowing up to some predetermined tolerable amount of change in the ITD information, and canceling one of the pulses or interaural pulse pairs to avoid time-overlap.

10. A method according to claim 9, wherein preserving the associated ITD information preferentially preserves lower frequency information over higher frequency information.

11. A binaural auditory prosthesis, comprising:
    at least one acoustic sensing module for generating binaural acoustic signals representing sound associated with a user's left and right ears respectively;
    at least one binaural stimulation module for generating corresponding binaural stimulation signals based on the binaural acoustic signals for electrical stimulation of auditory nerve tissue of the user, wherein the binaural stimulation signals each include a fine structure component with periodic characteristics and interaural time difference (ITD) information; and at least one interaural time difference (ITD) module for adding a phase jitter component to the binaural stimulation signals to reduce the periodic characteristics of the fine structure component while preserving the interaural time difference (ITD) information.

12. A binaural auditory prosthesis according to claim 11, wherein the fine structure component includes peaks reflecting the ITD information.

13. A binaural auditory prosthesis according to claim 11, wherein the fine structure component includes zero crossings reflecting the ITD information.

14. A binaural auditory prosthesis according to claim 11, wherein the ITD module adds the phase jitter component based on detecting a temporal event in the binaural acoustic signal.

15. A binaural auditory prosthesis according to claim 14, wherein the ITD module detects the temporal event based on a predetermined time delay-threshold associated with the binaural acoustic signal.

16. A binaural auditory prosthesis according to claim 14, wherein the ITD module detects the temporal event based on ITD information from one or more spectral channels associated with the binaural acoustic signal.

17. A binaural auditory prosthesis according to claim 11, wherein each stimulation signal includes information for a plurality of spectral channels.

18. A binaural auditory prosthesis according to claim 17, wherein the at least one binaural stimulation module generates the binaural stimulation signals so as to avoid a time-overlap between pulses from different spectral channels for the same side of hearing.

19. A binaural auditory prosthesis according to claim 18, wherein the at least one binaural stimulation module avoids time-overlap by at least one of shifting interaural pulse pairs in time within one channel while preserving the associated ITD information, shifting individual pulses while allowing up to some predetermined tolerable amount of change in the ITD information, and canceling one of the pulses or interaural pulse pairs to avoid time-overlap.

20. A binaural auditory prosthesis according to claim 19, wherein the at least one binaural stimulation module preserves the associated ITD information by preferentially preserving lower frequency information over higher frequency information.

* * * * *